US00PP23043P3

(12) United States Plant Patent
Eaton

(10) Patent No.: US PP23,043 P3
(45) Date of Patent: Sep. 18, 2012

(54) WEEPING REDBUD TREE NAMED 'PINK HEARTBREAKER'

(50) Latin Name: *Cercis canadensis*
Varietal Denomination: Pink Heartbreaker

(76) Inventor: Donald Eaton, Leesport, PA (US)

( * ) Notice: Subject to any disclaimer, the term of this patent is extended or adjusted under 35 U.S.C. 154(b) by 269 days.

(21) Appl. No.: 12/657,930

(22) Filed: Jan. 29, 2010

(65) Prior Publication Data

US 2011/0191921 P1 Aug. 4, 2011

(51) Int. Cl.
*A01H 5/00* (2006.01)

(52) U.S. Cl. ..... Plt./216

(58) Field of Classification Search ..... Plt./216
See application file for complete search history.

(56) References Cited

U.S. PATENT DOCUMENTS

PP10,328 P * 4/1998 Covey ..... Plt./216
PP18,528 P2 * 2/2008 Bennett ..... Plt./216

OTHER PUBLICATIONS

Anonymous. "new Weeing Redbud Debuts" "Today's Garden Center". Aug. 16, 2011. Available at: http://www.todaysgardencenter.com/news/varietycentral/?storyid=4536.*

* cited by examiner

*Primary Examiner* — Wendy C Haas
(74) *Attorney, Agent, or Firm* — James A. Lucas; Driggs, Hogg, Daugherty & Del Zoppo Co., LPA

(57) ABSTRACT

A new and distinct redbud tree named 'Pink Heartbreaker' is characterized by its strong weeping growth. This cultivar also exhibits vigorous growth throughout the growing season and striking clusters of pink flowers during the spring bloom. Like the parent plant, *Cercis canadensis*, 'Pink Heartbreaker' is disease and pest resistant.

4 Drawing Sheets

Latin name: *Cercis canadensis*.
Varietal denomination: 'PINK HEARTBREAKER'.

FIELD OF THE INVENTION

The present invention comprises a new and distinct cultivar of *Cercis canadensis* that was discovered among many seedlings in 2002 and is referred to by the cultivar name 'Pink Heartbreaker'.

BACKGROUND OF THE INVENTION

This new cultivar of *Cercis canadensis*, the 'Pink Heartbreaker' redbud, was originally discovered in a group of *Cercis canadensis* planted in a cultivated area at Leesport, Pa. Later dormant leaf buds of 'Pink Heartbreaker' were budded onto redbud rootstock in a controlled Environment. Buds taken from the limbs of these original 21 cloned plants were grafted onto rootstocks to produce new clones. The following spring some of the cloned plants were returned to Leesport, Pa. while the remainder of the cloned plants was used to produce more cloned plants through chip budding. Over the last three years, the clones of 'Pink Heartbreaker' have exhibited all of the same growing characteristics as the parent plant, and have come true to type through succeeding generations of asexual propagation.

SUMMARY OF THE INVENTION

The following characteristics in combination distinguish the new tree named 'Pink Heartbreaker' cultivar from other cultivars of *Cercis canadensis*.

The 'Pink Heartbreaker' cultivar has a distinctive weeping shape that the parent plant, *Cercis canadensis*, does not exhibit. Although two other cultivars of *Cercis canadensis* ('Covey' U.S. Plant Pat. No. 10,328 and 'Cascading Hearts', U.S. Plant Pat. No. 18,528) do exhibit weeping habit, they do not exhibit the vigorous growth that the 'Pink Heartbreaker' cultivar does.

'Pink Heartbreaker' cultivar also has distinctive, pink-color flowers that occur in large clusters. The stunning flowers and weeping growth habit of 'Pink Heartbreaker' cultivar will make it a popular tree for landscaping applications.

The 'Pink Heartbreaker' cultivar is cold tolerant. It has withstood very low 20 degree F. temperatures in late April, long after the leaf buds opened. Most trees in Middle Tennessee were severely damaged with the cold spell so late in the spring of 2007. Furthermore, upon the return to some of the clones to Leesport, Pa. in 2008, those cloned plants have grown vigorously and Leesport is in climate Zone 6a, USDA Plant Hardiness Zone Map.

The 'Pink Heartbreaker' cultivar is able to endure drastic changes in moisture levels. There is usually heavy rainfall in the spring and very little rain in July and August in Middle Tennessee (climate Zone 6b, USDA Plant Hardiness Zone Map). However, in 2007 and 2008 there was little rain in the spring and late summer, and the cultivar thrived. Furthermore, throughout the summer 2007 and 2008 many days broke the record high temperature for the day.

The 'Pink Heartbreaker' cultivar grows rapidly. The cloned plants over the last 3 years have grown to a height of 2.59 m (8.5 feet) growing approximately 0.91 to 1.22 m (3 to 4 feet) per year.

After 3 years of growth, the 'Pink Heartbreaker' cultivar has remained insect and pathogen resistant growing in the fields located at middle Tennessee. The original tree that was discovered in Leesport, Pa. in 2002, and the 21 cloned plants that were propagated in middle Tennessee and taken to Leesport, Pa. are also insect and pathogen resistant.

The 'Pink Heartbreaker' cultivar has not been observed under all possible conditions, and it is not known how the cultivar might respond to various conditions or other zones.

BRIEF DESCRIPTON OF THE DRAWINGS

The colored photographs illustrate the unique features of the new redbud tree. The color reproduction is as true as is reasonably possible using digital photography.

DETAILED DESCRIPTION OF THE INVENTION

Three characteristics distinguish 'Pink Heartbreaker' as a new and distinct cultivar. 1. Over the last eight years since, the cultivar, 'Pink Heartbreaker', was observed, it has exhibited a strong weeping growth unlike the *Cercis canadensis* seedling that grows upright and does not exhibit weeping growth. 2. The new cultivar 'Pink Heartbreaker' has vigorous growth. 3. The cultivar also has a striking cluster of pink flowers. These cultivars have been undergoing evaluation for the past 3 years.

The new cultivar, 'Pink Heartbreaker' exhibits new and distinctive shape, weeping, vigorous growth both in Leesport, Pa. and in middle Tennessee, and distinctive pink flower clusters along the branches. The cultivar exhibits a weeping shape unlike the parental redbud and the weeping is more pronounced than the weeping exhibited by the patented redbud cultivars known as 'Covey' and 'Cascading Hearts'. It reaches a height of 8.5 feet and 3.5 feet in width. 'Pink Heartbreaker' also has a more vigorous growth habit than other weeping redbud cultivars known to the inventor. All other growth characteristics of the cultivar are found to be similar to the parent plant, *Cercis canadensis*. Other clones of *Cercis canadensis* that have been observed have characteristics of *Cercis canadensis*. Only the clones that have originated from rootstock grafts of the original *Cercis canadensis* 'Pink Heartbreaker' exhibit the weeping habit and distinctive pink flower clusters attributed to the new cultivar, 'Pink Heartbreaker.' Over the last 3 years, only the grafted clones have exhibited these newly described characteristics.

Figure 1:
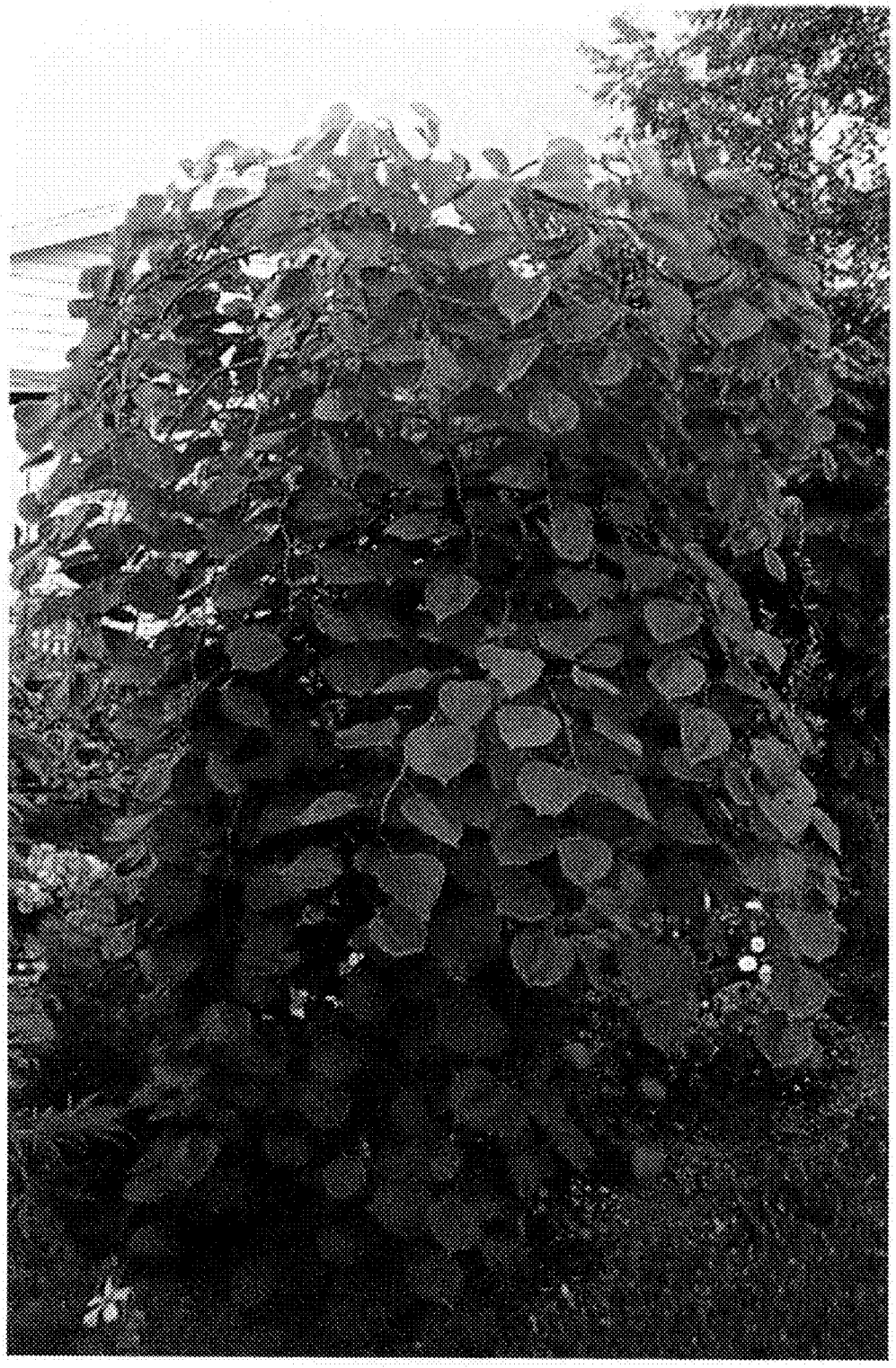
FIG. 1 shows the green, heart-shaped leaves on drooping branches of the Pink Heartbreaker in late spring-early summer. This cloned plant is one that was grafted on redbud rootstock in middle Tennessee.
Figure 2:
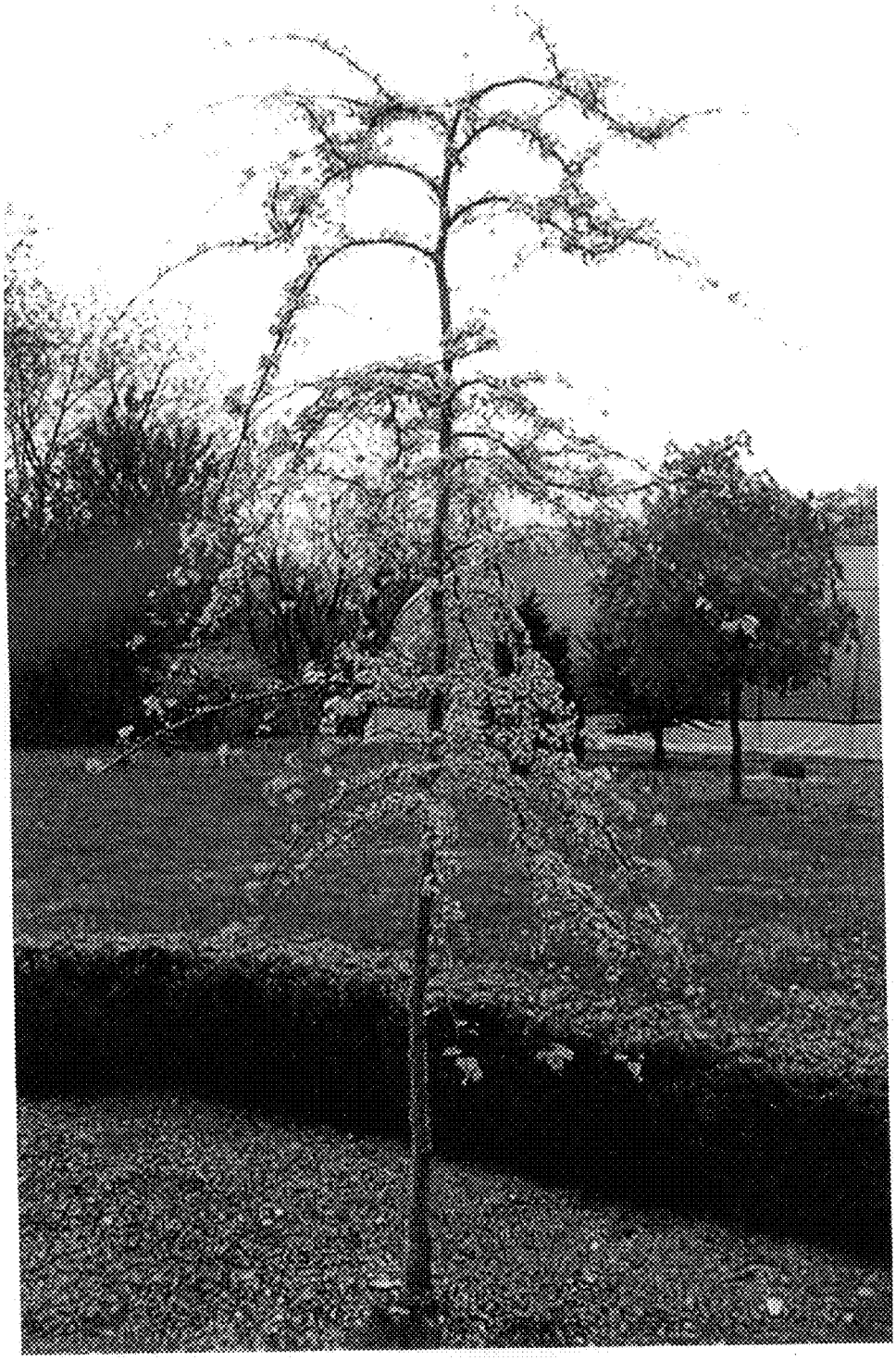
FIG. 2 shows flower color at the height of flower production.

As shown in the first two photographs (labeled FIG. 1 and FIG. 2) of the 'Pink Heartbreaker' cultivar shows the distinctive weeping habit of the tree. The branches droop in a characteristic weeping habit. The leaves exhibit the typical heart shape and remain green throughout the growing season and turn yellow in the fall. The photograph (FIG. 2) shows the tree in the dormant season with no foliage. Because the cultivar, and the parent plant that it came from, are deciduous, the leaves turn the color yellow and drop off each fall in Zone 6a, which includes Leesport, Pa. and in Zone 6b, which includes Middle Tennessee. The leaves are 5 cm to 10 cm in length and 6 cm to 15 cm in width. Thus, they are generally slightly wider than they are long. The leaves have smooth margins. The petioles are a dark purple-brown (RHS 187A, plate 55) initially when the leaf first opens but turn green (RHS 139C, plate 42) within several weeks. The diameter of petioles is 1.0 to 1.5 mm and varies in length from 3.5 cm to 4.5 cm on mature leaves. Branching on 'Pink Heartbreaker' is an alternate arrangement.

Figure 3:
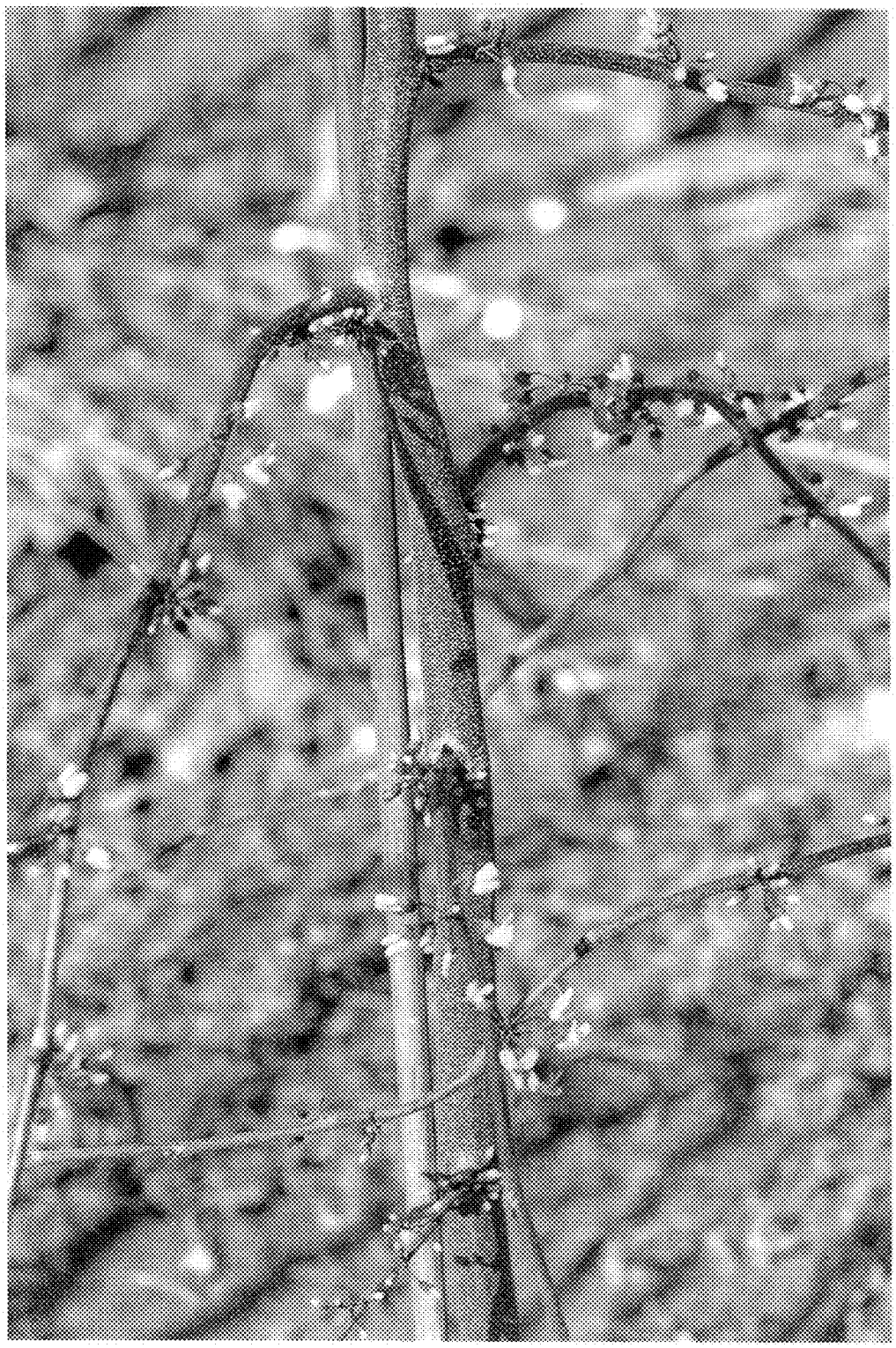
FIG. 3 shows a closer view of the flower color at the height of flower production. The flower exhibits a distinctive pink color, and the flowers generally occur in clusters.
Figure 4:
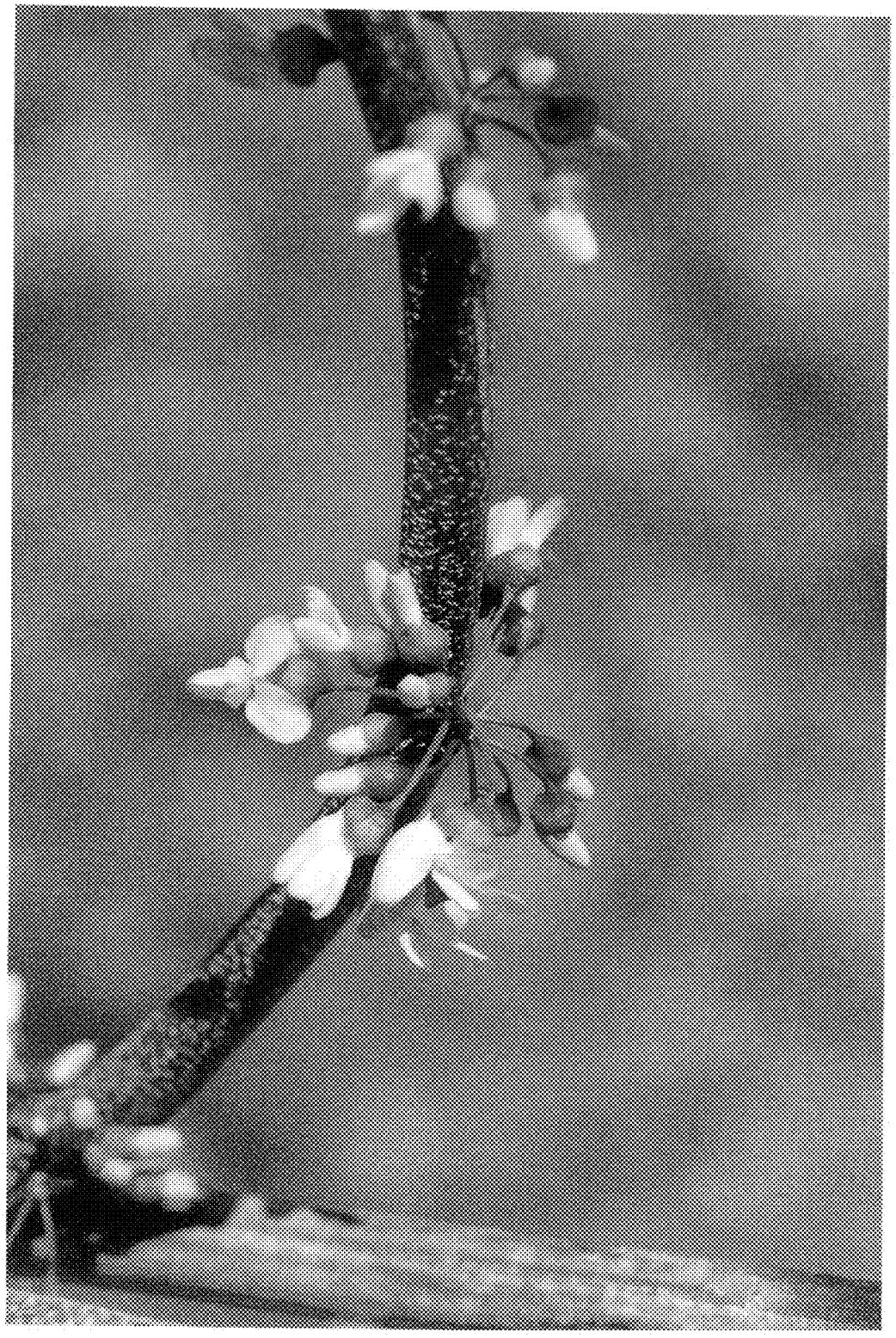
FIG. 4 is an enlarged view of the flower clusters shown in FIG. 3.

In the third and fourth photographs (FIGS. 3 and 4 taken in April of the year) the flower clusters are seen. While the flowers on some branches are single, many are in clusters. The flowers have soft, distinctive pink petals.

The 'Pink Heartbreaker' cultivar has proven to be both drought resistant and very winter hardy. In the April 2007, Middle Tennessee experienced an unusually late freeze during which the overnight temperatures dropped into the low 20s F. This was a particularly dangerous and damaging freeze because most of the trees had already broken dormancy. The 'Pink Heartbreaker' cultivar survived this freeze and continued to produce foliage throughout the spring and summer months. All grafts taken from the plants exhibit the same rapid growth that has been observed for the last 3 growing seasons that the 'Pink Heartbreaker' cultivar has been cultivated. The clones that were returned to Leesport, Pa. in 2008 have grown vigorously. Thus, the 'Pink Heartbreaker' is a hearty redbud that grows vigorously and can withstand late freezes and severe droughts.

The 'Pink Heartbreaker' cultivar can also endure drastic changes in moisture. 'Pink Heartbreaker' cultivar has been successfully grown without irrigation after it was moved into the fields during its second season in middle Tennessee. Each summer since it was rooted in 2006, it has endured the drought that middle Tennessee has experienced during the months of July and August. Middle Tennessee usually experiences heavy rainfalls during the spring; however, immediately after the late spring 2007 freeze, Middle Tennessee experienced a 2 month drought. While many annuals, perennials, shrubs, and trees were severely damaged or killed by the late spring freeze that was followed by a 2-month drought, the 'Pink Heartbreaker' cultivar survived and demonstrated itself to be cold and drought tolerant.

The 'Pink Heartbreaker' cultivar has been successfully propagated asexually. The proven means of asexual propagation has been chip budding to redbud rootstock. The 'Pink Heartbreaker' cultivar was discovered in Leesport, Pa. in 2002. The cultivar has retained all the characteristics of the original selected seedling found in 2002. It has been successfully propagated through several generations of asexual reproduction with a survival rate between 77% the first year to a survival rate of 100% last year. Each generation has been stable and produced true-to-type plants each and every time that the plant has been propagated.

The unique weeping habit and vigorous rapid growth (0.61 to 1.22 m or 2 to 4 feet per year) and distinctive, pink flower clusters of 'Pink Heartbreaker' cultivar make it well suited for a variety of landscaping uses. Furthermore, the 'Pink Heartbreaker' cultivar is cold and drought tolerant. The cultivar is a small size tree that exhibits beautiful clusters of pink flowers early in the spring. As the flowers fade, leafbuds open to heartshaped leaves. In the fall the leaves turn yellow. The vigorous growth habit of this weeping redbud known as 'Pink Heartbreaker' should make it a popular redbud.

BOTANICAL DESCRIPTION

The following observations, measurements, and values describe plants grown in middle Tennessee. The actual appearance and characteristics of any individual plant will vary due to horticultural practices and local conditions. The tree used for this description is three years old. Color references are made to The Royal Horticultural Society (R.H.S.) Colour Chart (Published 2005) except where terms of ordinary significance are used.

Botanical classification: *Cercis canadensis*.

Commercial classification: 'Pink Heartbreaker' redbud.

Origin: Found in Leesport, Pa. and propagated on redbud rootstock in middle, Tennessee.

Parentage: Cutting of stems from *Cercis canadensis*.

Propagation: Asexual by chip budding to rootstock.

Plant:

*Growth rate*.—Fast; an average of 4 to 6 feet per year in the nursery, perhaps 2 to 3 feet in the landscape.

*Form*.—Oval, slightly wider at the top of the plant.

*Shape*.—Weeping habit. The weeping habit is more pronounced and more graceful than that of 'Covey' which has a more pronounced zig zag pattern. The plant is broader with a fuller crown and more foliage during the growing season than the other weeping cultivars.

*Height*.—Average size tree, probably from 2.5 to 3.0 meters (or 8 to 10 feet) in three years, with more growth expected with age.

*Spread*.—A three year tree has a spread of approximately 42". The spread of the mature tree is unknown at this time.

*Density*.—Thick with foliage.

*Trunk Size*.—2.0 to 3.0 cm in diameter at the base of the trunk at ground level after the first year. After two years, the diameter of the trunk is 2.5 to 3.0 cm measured 12 inches (0.305 m) off the ground. The tree trunk is estimated to grow approximately 0.7 cm (½ inch) per year in the landscape. This rate of growth, both in branching and trunk caliper, is much more vigorous than that of 'Covey' and 'Cascading Hearts'.

*Bark—(trunk)*.—Smooth, color is brown (RHS N199A, plate 47) textured with tiny raised lenticels.

*Branching arrangement*.—Alternate. Angle of attachment of branching off the trunk: Ranges from 30 to 45 degrees but bends back or weeps as the stem extends from the truck. The elbow characteristic of 'Covey' is absent in the present cultivar. Sunscald damage to the bark in the crown is avoided due to fuller foliage cover in the crown. The branch structure is more durable and less likely to break during routine harvesting and shipping than other cultivars.

*Stem*.—Typical observed length is up to 50 to 55 cm or more on branches 1.5 m (or 5 feet) off the ground, diameter of one-year old branches varies from 1.1 cm to 1.3 cm. On the new growth the stem color is green (RHS 144A, plate 41). The diameter of the new growth stem near the apical meristem averages 0.5 cm. The arrangement of leaves is opposite. The internodal length on the stem varies from 4.0 cm to 7.0 cm. with an average being 5.0 cm.

*Lenticels*.—Small, but conspicuous, silver, 1.5 to 3.0 mm in length and 0.1 mm in width.

*Leaves*.—Deciduous.

*Leaf length*.—Petiole 3.5 cm to 4.5 cm, average 4.0 cm. The color of the petiole is (RHS 139C, plate 42) and has an average diameter of 1.25 mm (range is 1.0 to 1.5 mm).

*Average leaf width*.—From 5 cm to 15 cm.

*Leaf shape*.—Heart shaped.

*Leaf margin*.—Smooth.

*Leaf texture*.—Smooth on the upper and lower surfaces of the leaf, the lower surface has some hairs.

*Leaf quantity*.—Abundant.

*Leaf size*.—Approximately 25% to 30% larger than that of 'Cascading Hearts'.

*Leaf color*.—Upper side: The newly emergent leaf exhibits a reddish green color for 5 to 7 days. Within a week the red fades and the color of 5 to 6-week old leaves is green (RHS 137C, plate 42). Lower side: the color is a lighter green (RHS 139C, plate 42).

*Leaf ribs and veins*.—Upper rib surface color is green (RHS 145C, plate 44), lower rib surface color is a light green (RHS 145B, plate 44), pattern of venation is palmate.

*Vegetative buds*.—Terminal bud is oval. It is 5-7 mm in length and 2 mm in width.

*Leaf apex*.—Acute.

*Base descriptor*.—Cordate.

Flowers:

*Dormant flower buds*.—Terminal, buds are 0.2 cm to 0.3 cm in length and 0.1 cm in width.

*Flower*.—Petals of the open flower are a maroon-red or purple. (53A RHS, plate 53). The flowers are lighter in color and closer to pink than the color of either 'Covey' or 'Cascading Hearts'.

*Sepals*.—On bud are brown (RHS 183A, plate 54).

*Fragrance*.—None perceptible.

*Blooming season*.—From late March until mid-April in Middle Tennessee.

*Bloom duration*.—From 2 to 3 weeks on the plant.

*Stamens*.—Yellow — 10 per flower.

*Flower arrangement*.—In a tight cluster.

*Pollen amount*.—Abundant.

*Pollen color*.—Yellow.

*Pistils*.—Not observed.

*Anther*.—10 per flower, they are yellow.

*Stigma*.—Not observed.

Seeds: No seed pods have been observed in the nursery, unlike the cultivar 'Covey'. In the landscape, very limited seed production in comparison with similar age and sized seedling plants.

Fruit: Flat legume pod, 2 to 4 inches (5-10 cm) in length.

Peduncles: 1.0 to 1.5 cm.

Disease and pest resistance: No known susceptibility to diseases or pests common to Cercis canadensis.

What is claimed is:

1. A new and distinct cultivar of *Cercis canadensis* tree named 'Pink Heartbreaker' as illustrated and described herein.

* * * * *